US00PP13516P2

(12) United States Plant Patent
Lemon

(10) Patent No.: US PP13,516 P2
(45) Date of Patent: Jan. 28, 2003

(54) GERANIUM PLANT NAMED 'PATRIOT RED'

(75) Inventor: David Lemon, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,132

(22) Filed: Jun. 8, 2001

(51) Int. Cl.[7] ..... A01H 5/00

(52) U.S. Cl. ..... Plt./330

(58) Field of Search ..... Plt./330

*Primary Examiner*—Bruce R. Campell
*Assistant Examiner*—Annette H. Para
(74) *Attorney, Agent, or Firm*—Webb Ziesenheim Logsdon Orkin & Hanson, P.C.

(57) ABSTRACT

A new and distinct zonal geranium plant with reddish colored flowers above medium green foliage having distinct zones and continuous and early flowering.

1 Drawing Sheet

CLASSIFICATION

*Pelargonium×hortorum* (zonal geranium).

VARIETAL DENOMINATION

'Patriot Red'.

BACKGROUND OF THE INVENTION

The present invention comprises a new and distinct cultivar of *Pelargonium×hortorum* known by the varietal name 'Patriot Red', Breeder No. 7DG4774-1. The new variety was discovered in Lompoc, Calif. The new variety is a result of cross breeding of Grand Prix (female) (unpatented) and Seedling Red #3824 (male) (unpatented). The new variety exhibits similar flower color to its parents, but differs in its improved plant habit and heat tolerance. The new variety has more distinct leaf zonation and shorter flower stems than most other varieties in its market class. The new variety was first asexually reproduced by cuttings in Lompoc, Calif. The new variety has been trial and field tested and has been found to retain its distinctive characteristics and remain true to type through successive propagations.

The new variety, when grown in a glass greenhouse in Connellsville, Pa. using full light, 60° F. night temperature and 68° F. day temperature and grown in a soilless media with constant fertilizer at 200–250 ppm nitrogen and potassium has a response time of six weeks to flowering from a rooted cutting to flowering in a 10 cm pot.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar at 9 weeks grown from a rooted cutting. The data which defines these characteristics were collected by asexual reproductions carried out at Oglevee, Ltd. in Connellsville, Pa. The color readings on a plant in a 4 inch pot were taken on May 9, 2000 indoors under 200–220 foot candles of cool white fluorescent light. Color references are primarily to The R.H.S. Colour Chart of The Royal Horticultural Society of London.

PLANT

Form: Medium mound.
Height from media surface: 15–20 cm.
Growth: Free basal branching.
Strength: Does not require artificial support.
Response time: 14–21 days to visible root.
Foliage: Stalked leaf attachment with significantly visible zones.
Leaves:
- *Size.*—6.0–7.2 cm long; 7.7–8.3 cm wide.
- *Shape.*—Reniform; cordate base.
- *Margin.*—Crenate.
- *Texture.*—Pubescent.
- *Color.*—Upper surface: Green Group 137A with zone of Brown Group 200A. Lower surface: Green Group 138B.
- *Ribs and veins.*—Type: Palmate. Color: Yellow-Green Group 145A.

Petioles:
- *Color.*—Yellow-Green Group 144A.
- *Length.*—8.0–10.5 cm.

Stem:
- *Color.*—Yellow-Green Group 144A.
- *Internode length.*—2.5–3.5 cm.

THE BUD

Shape and size when just showing color, with three individual buds having significant color and just about ready to open:
- *Overall.*—Semi-spherical.
- *Individual bud.*—Round-elliptical.
- *Umbel.*—4.0 cm.
- *Individual bud.*—0.7–0.9 cm wide; 1.0–1.5 cm long.

INFLORESCENCE

Blooming habit: Continuous; early flowering.
Size of umbel: 10–12 cm.
Size of fully open bloom: 4.5–5.5 cm wide; 1.0–1.5 cm deep.

Borne: Flowers on pedicel; pedicel on peduncle; 6–10 cm above foliage.

Number of flowers per umbel: 10–27.

Flowers:

*Form.*—Open flat to slightly cupped, petals tilt upward and curl giving a ruffled effect, petals overlap.

*Petals.*—Size: 2.0–2.5 cm wide; 2.5–2.7 cm long. Number per floret: 8–9. Margin: Complete. Shape: Round at edge, drawn out to narrower base. Color: Upper surface: Red Group 44A at outer edge moving to Red Group 40B and Orange-Red Group 33A toward center, and Red Group 40C toward base. Base of petals is white. Some petals have darker veining of Red Group 46B. Lower surface: Red Group 41B, some have slight edge of Red Group 43C at outer edge.

*Texture.*—Highly reflective; smooth.

*Tonality from a distance.*—Bright orange-red with highly reflective qualities giving each flower a wide range of red tones and depth.

Petaloids:

*Number.*—0–6.

*Shape.*—Irregular; some tubular, some petal like, but crinkled, some with cut edges, others anther-like holding pollen.

*Color.*—Same as petals.

Pedicel:

*Length.*—2.5–2.8 cm.

*Color.*—Greyed-Purple Group 187B at base of flower moving to Greyed-Purple Group 185B and Yellow-Green Group 145A at very base.

Peduncle:

*Length.*—13–18 cm.

*Color.*—Yellow-Green Group 144A.

Disease/pest resistance: No unusual susceptibility to diseases or pests has been noted to date.

Lasting quality: Individual flowers and umbels will last 7–14 days.

Fragrance: None.

REPRODUCTIVE ORGANS

Stamens:

*Quantity.*—3–7, often attached to petaloids.

*Anthers.*—0.2–0.3 cm.

*Filaments.*—Length: 1.0–1.2 cm. Color: White with peach-orange tips.

*Pollen color.*—Orange.

Pistils:

*Number.*—One.

*Length.*—0.9 cm.

*Stigma.*—Number: One. Color: Red.

*Style.*—Length: 0.4–0.5 cm. Color: Red.

Ovaries:

*Color.*—Green.

*Length.*—0.5 cm.

*Width.*—0.2–0.3 cm.

*Pubescence.*—Very pubescent.

*Completeness.*—Superior.

Fruit: None observed.

I claim:

1. A new and distinct variety of zonal geranium plant substantially as shown and described.

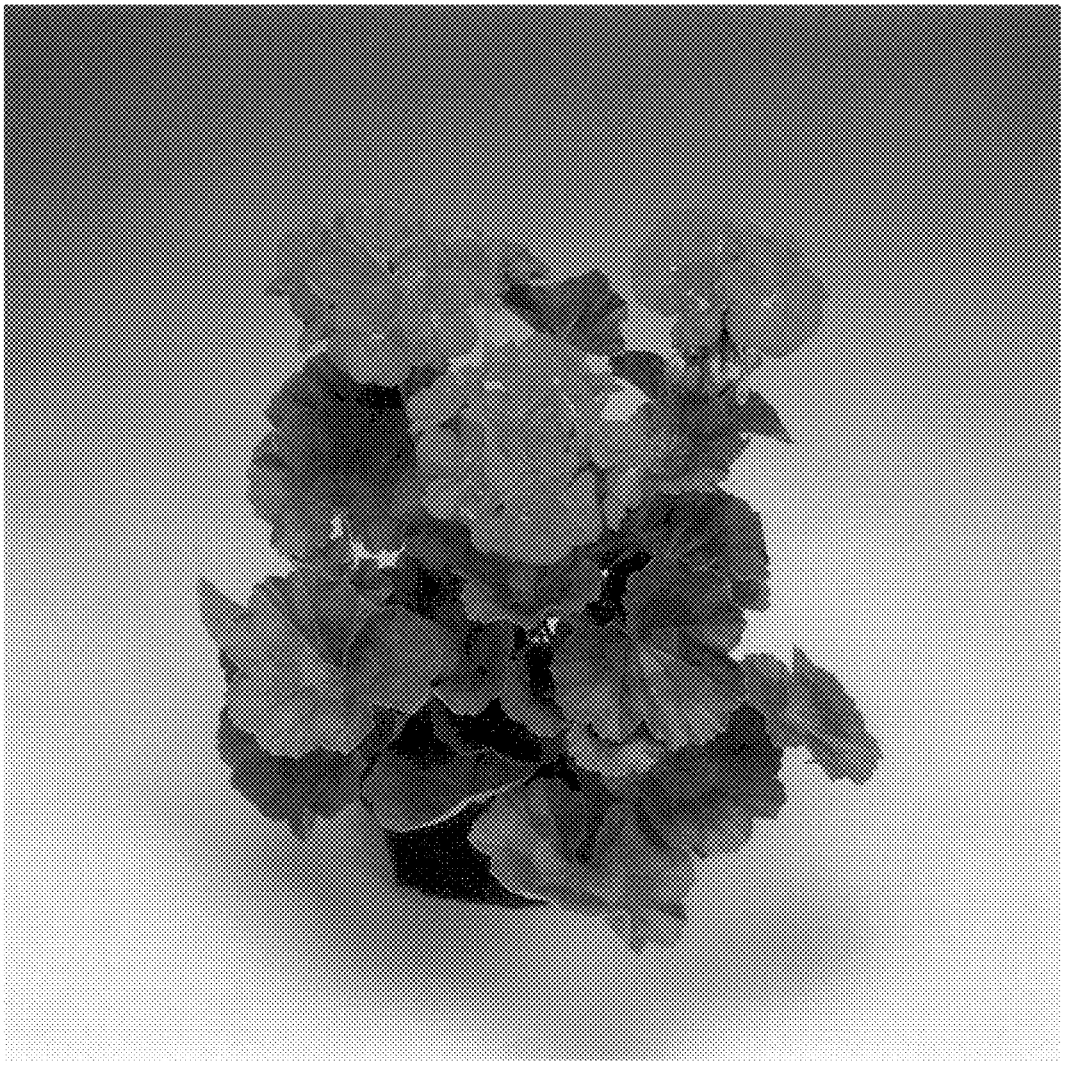

* * * * *